(12) United States Patent
Matsumura et al.

(10) Patent No.: US 7,414,136 B2
(45) Date of Patent: Aug. 19, 2008

(54) METHOD FOR PRODUCING 3-SUBSTITUTED 2-CHLORO-5-FLUORO-PYRIDINE OR ITS SALT

(75) Inventors: Yasushi Matsumura, Ichihara (JP); Nobuaki Mori, Ichihara (JP); Yasuhiro Yamada, Ichihara (JP)

(73) Assignee: Asahi Glass Company, Limited, Tokyo (JP)

( * ) Notice: Subject to any disclaimer, the term of this patent is extended or adjusted under 35 U.S.C. 154(b) by 158 days.

(21) Appl. No.: 11/265,179

(22) Filed: Nov. 3, 2005

(65) Prior Publication Data

US 2006/0058529 A1    Mar. 16, 2006

Related U.S. Application Data

(63) Continuation of application No. PCT/JP2004/006267, filed on Apr. 30, 2004.

(30) Foreign Application Priority Data

May 9, 2003    (JP) ............................ 2003-132137

(51) Int. Cl.
*C07D 213/85* (2006.01)
*C07D 213/80* (2006.01)

(52) U.S. Cl. ................. 546/318; 546/286; 546/316

(58) Field of Classification Search ............. 546/316, 546/321, 286, 318
See application file for complete search history.

(56) References Cited

U.S. PATENT DOCUMENTS 5,250,548 A    10/1993 Winn et al.

FOREIGN PATENT DOCUMENTS

| EP | 0254982 | * | 7/1987 |
| EP | 634413 | | 1/1995 |
| WO | WO 98/50362 | | 11/1998 |

OTHER PUBLICATIONS

Winn et. al., "2-(Alkylamino)nicotinic Acid and Analogs. Potent Angiotensin II Antagonists", J. Med. Chem. 1993, 36, 2676-2688.*

Setliff et al, J. Chemical and Engineering Data, 1972, vol. 17, No. 4, pp. 515-516.

* cited by examiner

*Primary Examiner*—Patricia L Morris
(74) *Attorney, Agent, or Firm*—Oblon, Spivak, McClelland, Maier & Neustadt, P.C.

(57) ABSTRACT

To provide a method for producing a 3-substituted 2-chloro-5-fluoro-pyridine or its salt in high yield from a readily available material through a short process under mild reaction conditions using a reagent which is easy for handling and simple in the reaction operation. Namely, a method for producing the following compound (2) or its salt which comprises selectively reducing a chlorine atom at the 6-position of the following compound (1) or its salt, is provided. Further, a method for producing the following compound (4) or its salt which comprises substituting a $Z^1$ group of the following compound (2) or its salt obtained by the reduction reaction, by a $Z^2$ group, is provided. Here, $Z^1$ is —$CO_2R^1$, etc., and $R^1$ is a hydrogen atom, an alkyl group, an alkenyl group, an aryl group, an aralkyl group or a cycloalkyl group. $Z^2$ is a group different from $Z^1$ and is —$CO_2R^5$, etc., and $R^5$ is an alkyl group, an alkenyl group, an aryl group, an aralkyl group or a cycloalkyl group.

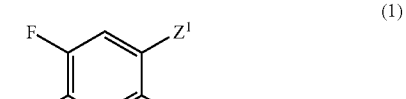

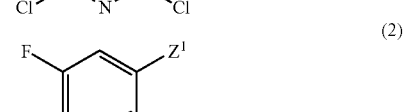

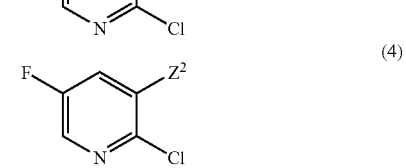

26 Claims, No Drawings

METHOD FOR PRODUCING 3-SUBSTITUTED 2-CHLORO-5-FLUORO-PYRIDINE OR ITS SALT

TECHNICAL FIELD

The present invention relates to a novel method for producing a 3-substituted 2-chloro-5-fluoro-pyridine or its salt, such as 2-chloro-5-fluoronicotinic acid or its salt. The 3-substituted 2-chloro-5-fluoro-pyridine or its salt is a compound useful as an intermediate for pharmaceuticals or for agricultural chemicals and further as an intermediate or the like for production of various functional materials.

BACKGROUND ART

With respect to a method for producing a 3-substituted 2-chloro-5-fluoro-pyridine or its salt, the following methods have heretofore been proposed.

(1) A method wherein 2,6-dichloro-5-fluoronicotinic acid is used as the starting material, and it is converted to an ethyl ester of 2,6-dichloro-5-fluoronicotinic acid and then reacted with sodium thiomethoxide to obtain ethyl 2-chloro-5-fluoro-6-methylthionicotinate, and further, the methylthio group at the 6-position is reduced in the presence of a Raney nickel catalyst to obtain ethyl 2-chloro-5-fluoro-nicotinate (U.S. Pat. No. 5,250,548 (Examples 180A to C)).

(2) A method wherein 2-hydroxy nicotinic acid is used as the starting material, and the 5-position is nitrated, then the 2-position is chlorinated, then the nitro group at the 5-position is reduced in hydrochloric acid by means of tin(II) chloride to obtain 5-amino-2-chloronicotnic acid hydrochloride, which is then diazotized by means of tetrafluoroboric acid and sodium nitrite to convert the 5-position to diazonium tetrafluoroborate, followed by thermal decomposition in 1,2-dichlorobenzene to obtain 2-chloro-5-fluoronicotinic acid (European Patent No. 634413A1 (pages 12 and 13)).

(3) A method wherein 2-chloro-3-methyl-5-nitropyridine is used as the starting material, and the nitro group is reduced and then diazotized in $HPF_6$ to convert the 5-position to diazonium hexafluorophosphate, followed by thermal decomposition to obtain 2-chloro-5-fluoro-3-methylpyridine, which is further oxidized with potassium permanganate to obtain 2-chloro-5-fluoronicotinic acid (Frank L. Setliff, Gary O. Rankin, "J. Chemical and Engineering Data", (U.S.A.), 1972, Vol. 17, No. 4, p. 515).

However, the above-methods have the following drawbacks.

In the method (1), the reaction for introducing a methylthio group is a reaction accompanying a bad odor. Further, in that method, after substituting a hydrogen atom by a methylthio group, the methylthio group is again substituted to a hydrogen atom by a reduction reaction, and as such; the method is inefficient. Further, there is an additional drawback that the yield in such a reduction reaction is low at a level of 30%. The method (2) has a drawback that the reaction process is long. Further, after synthesizing an unstable diazonium salt, the diazonium salt is thermally decomposed at a high temperature, and accordingly, the method has a drawback that the overall yield is low. The method (3) also has a drawback that the reaction process is long. Further, it has a drawback that the yield in the oxidation reaction is so low that the method is poor in practical applicability.

DISCLOSURE OF THE INVENTION

The present invention has been made to solve the above problems and to provide a method for producing in good yield a 3-substituted 2-chloro-5-fluoro-pyridine or its salt which is useful as e.g. an intermediate for production of pharmaceuticals, agricultural chemicals and various functional materials, from a starting material which is industrially readily available, through a short process under mild reaction conditions using a reagent which is easy in handling and simple in the reaction operation.

Namely, the present invention provides the following.

(1) A method for producing a compound represented by the following formula (2) or its salt, which comprises selectively reducing a chlorine atom at the 6-position of a compound represented by the following formula (1) or its salt, provided that in the following formulae, $Z^1$ is a group represented by $—CO_2R^1$, $—CONR^2R^3$ or $—CN$, wherein each of $R^1$, $R^2$ and $R^3$ which are independent of one another, is a hydrogen atom, an alkyl group, an alkenyl group, an aryl group, an aralkyl group or a cycloalkyl group:

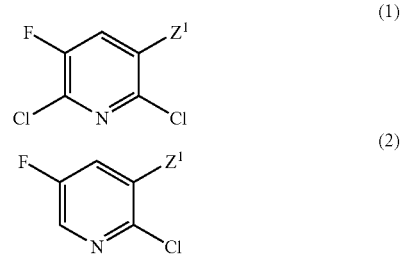

(2) A method for producing a compound represented by the following formula (2), which comprises selectively reducing a chlorine atom at the 6-position of a compound represented by the following formula (1), provided that in the following formulae, $Z^1$ is a group represented by $—CO_2R^1$, $—CONR^2R^3$ or $—CN$, wherein each of $R^1$, $R^2$ and $R^3$ which are independent of one another, is a hydrogen atom, an alkyl group, an alkenyl group, an aryl group, an aralkyl group or a cycloalkyl group:

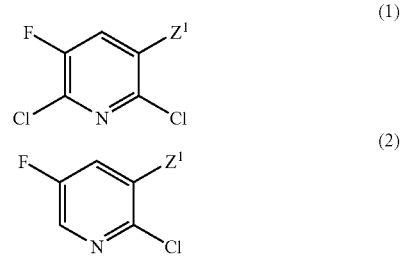

(3) The method according to (1) or (2), wherein $Z^1$ is $—CO_2R^1$ (wherein $R^1$ is as defined above).

(4) The method according to any one of (1) to (3), wherein the reduction is carried out by letting a protic solvent act in the presence of a metal or a metal salt.

(5) The method according to any one of (1) to (4), wherein the reduction is carried out by letting a protic solvent act in the presence of zinc.

(6) A method for producing a compound represented by the following formula (4) or its salt, which comprises carrying out a substitution reaction of a compound represented by the formula (2) or its salt obtained by the method as defined in any one of (1) to (5), to substitute the $Z^1$ group at the 3-position by a $Z^2$ group, thereby to obtain a compound represented by the following formula (4) or its salt, provided that $Z^2$ in the following formula is a group different from $Z^1$ and is a group represented by —$CO_2R^5$, —$CONR^6R^7$ or —CN, wherein $R^5$ is an alkyl group, an alkenyl group, an aryl group, an aralkyl group, or a cycloalkyl group, and each of $R^6$ and $R^7$ which are independent of each other, is a hydrogen atom, an alkyl group, an alkenyl group, an aryl group, an aralkyl group or a cycloalkyl group:

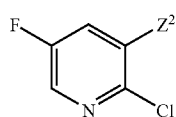

(4)

(7) The method according to (6), wherein from the compound of the formula (2) or its salt wherein the $Z^1$ group is a group represented by —COOH or —$COOR^{10}$ (wherein $R^{10}$ is an alkyl group), the compound (4) wherein $Z^2$ is a —$COOR^5$ group (wherein $R^5$ is as defined above), is obtained by an esterification reaction in a case where $Z^1$ is a —COOH group, or by an ester exchange reaction in a case where $Z^1$ is a —$COOR^{10}$ group (wherein $R^{10}$ is as defined above).

BEST MODE FOR CARRYING OUT THE INVENTION

In this specification, the compound represented by the formula (1) may be referred to also as the compound (1). The same applies to other compounds.

In this specification, "an alkyl group" may be linear or branched. Unless otherwise specified, the alkyl group is preferably a $C_{1-6}$ lower alkyl group. As an example of the alkyl group, a methyl group, an ethyl group, a n-propyl group, an isopropyl group a butyl group, an isobutyl group, a sec-butyl group, a tert-butyl group, a pentyl group or a hexyl group may, for example, be mentioned.

"An alkenyl group" may be linear or branched. Unless otherwise specified, the alkenyl group is preferably a $C_{2-6}$ alkenyl group. As an example of the alkenyl group, an allyl group, an isopropenyl group or a 3-butenyl group may, for example, be mentioned.

"An aryl group" means a monovalent aromatic hydrocarbon group, and a phenyl group is preferred.

"An aralkyl group" means an alkyl group substituted by an aryl group. As the aryl group moiety, a phenyl group is preferred. Further, as the alkyl group moiety in the aralkyl group, a $C_{1-4}$ alkyl group is preferred. As an example of the aralkyl group, a benzyl group, a benzhydryl group, a trityl group or a phenylethyl group may, for example, be mentioned.

"A cycloalkyl group" means an at least 3-membered cyclic alkyl group, and a 3- to 8-membered cycloalkyl group is preferred. As an example of the cycloalkyl group, a cyclopentyl group, a cyclohexyl group or a cycloheptyl group may, for example, be mentioned.

In the compound (1) or its salt, $Z^1$ is a group represented by —$CO_2R^1$, —$CONR^2R^3$ or —CN, preferably —$CO_2R^1$ or —CN from the viewpoint of availability, particularly preferably —$CO_2R^1$ from the viewpoint of the yield and the efficiency in the post treatment after the reaction. Here, each of $R^1$, $R^2$ and $R^3$ which are independent of one another, is a hydrogen atom, an alkyl group, an alkenyl group, an aryl group, an aralkyl group or a cycloalkyl group. $R^1$ is preferably a hydrogen atom or a lower alkyl group, more preferably a hydrogen atom, a methyl group or an ethyl group, particularly preferably a hydrogen atom. Each of $R^2$ and $R^3$ which are independent of each other, is preferably a hydrogen atom, a methyl group or an ethyl group. It is particularly preferred that both $R^2$ and $R^3$ are hydrogen atoms, methyl groups or ethyl groups.

The compound (1) as the starting material in the present invention is commercially available or can easily be obtained by a usual preparation method. For example, it can be produced by the method disclosed in e.g. European Patent 333020 or U.S. Pat. No. 5,204,478. As the compound (1), one having a purity usually available may be used as it is without carrying out purification or the like. A salt of the compound (1) is commercially available or can easily be obtained by a usual preparation method. As such a salt, one having a purity usually available may be used as it is without carrying out purification or the like.

The following compounds may be mentioned as specific examples of the compound (1).

2,6-Dichloro-5-fluoronicotinic acid, methyl 2,6-dichloro-5-fluoronicotinate, ethyl 2,6-dichloro-5-fluoronicotinate, isopropyl 2,6-dichloro-5-fluoronicotinate, butyl 2,6-dichloro-5-fluoronicotinate, 2,6-dichloro-5-fluoronicotinonitrile, 2,6-dichloro-5-fluoronicotinic acid amide, 2,6-dichloro-5-fluoronicotinic acid dimethylamide, 2,6-dichloro-5-fluoronicotinic acid diethylamide, and 2,6-dichloro-5-fluoro-3-cyanopyridine. As the compound (1), 2,6-dichloro-5-fluoronicotinic acid is preferred since it is readily available and easy to handle.

The salt of the compound (1) may, for example, be a hydrochloride, a nitrate, a sulfate, an acetate, a formate, a trifluoroacetate or a phosphate, of the above compound.

In the present invention, the chlorine atom at the 6-position of the compound (1) or its salt is selectively reduced. For such a reduction reaction, conditions for a common reduction reaction may be employed. For example, the method for reducing the carbon-halogen bond as disclosed in "Shin Jikken Kagaku Kouza (New Experimental Chemistry) 14-Yukikagoubutsu no Gousei to Hannou (Syntheses and reactions of organic compounds) (I), published by Maruzen" may, for example, be employed. The reduction reaction of the present invention can be carried out under usual reduction reaction conditions, but only the 6-position is selectively reduced among chlorine atoms at the 2- and 6-positions. As a specific example for such a reduction reaction, any one of the following methods 1, 2 and 3 is preferred.

Method 1: A method wherein catalytic hydrogenolysis is carried out by using hydrogen in the presence of a metal reduction catalyst such as 5% Pd/calcium carbonate (one poisoned with lead, so-called Lindlar catalyst), Pd-barium sulfate, Pd—C, or Raney nickel.

In this method 1, the amount of the metal reduction catalyst is preferably from 0.1 to 100 mass %, particularly preferably from 1 to 30 mass %, based on the compound (1) or its salt. Further, the amount of hydrogen is preferably at least 1 time by mol, more preferably from 1 to 100 times by mol, particularly preferably from 1 to 10 times by mol, relative to the compound (1).

Method 2: A method wherein reduction is carried out by letting a protic solvent act in the presence of an alkali metal such as sodium or lithium; a metal such as magnesium, aluminum, tin, copper, zinc, iron or nickel, or an alloy thereof; or a metal salt such as lithium iodide or tin(II) chloride.

In the method 2, it is preferred to employ a metal, particularly a metal in a powder form. Further, as the metal, tin, copper, zinc or iron is, for example, preferred, and zinc is particularly preferred.

In the method 2, the amount of the metal or metal salt is preferably from 0.1 to 1,000 mass %, particularly preferably from 0.2 to 300 mass %, based on the compound (1) or its salt. Further, the amount of the protic solvent is preferably an amount whereby the compound (1) or its salt can be dissolved, dispersed or suspended, and it is preferably from 0.5 to 100 times by mass, particularly preferably from 1 to 10 times by mass, relative to the compound (1) or its salt.

The protic solvent in the method 2 is a compound which will be a hydrogen source in the reduction reaction and is a compound capable of being a solvent in the reaction of the present invention. As such a protic solvent, various solvents may be employed which are useful for reduction reactions. For example, water, an acid (hereinafter an acid as a protic solvent will be referred to as an acid (A)), an alkaline aqueous solution, an alcohol solvent, an ester solvent, a hydrocarbon solvent, an ether solvent, or a solvent mixture thereof, may, for example, be employed. As a specific example of such a solvent, an acid (A) such as acetic acid, formic acid, propionic acid or hydrochloric acid; an alcohol solvent such as methanol, ethanol, 2-propanol or t-butanol; or an aqueous alkaline solution such as an aqueous sodium hydroxide solution or an aqueous potassium hydroxide solution, may be mentioned. The protic solvent is preferably an acid selected from acetic acid, formic acid and hydrochloric acid, or an aqueous solution of such an acid; an alcohol solvent such as methanol, ethanol, 2-propanol or t-butanol; a solvent mixture having an acid (A) such as acetic acid, formic acid, propionic acid or hydrochloric acid, added to such an alcohol solvent, particularly preferably methanol, or a solvent mixture of methanol with acetic acid.

In a case where a solvent mixture having two or more solvents mixed, is used as the protic solvent, such solvents may preliminarily be mixed, or the respective solvents may separately be added to the reaction system and mixed in the reaction system to form a solvent mixture. In a case where the solvent mixture is a solvent mixture of an alcohol solvent with an acid (A), the acid (A) is preferably added lastly to the reaction system to form a solvent mixture, whereby the operation efficiency will be good.

The amount of the protic solvent is preferably from 0.5 to 50 times by mass, particularly preferably from 2 to 10 times by mass, relative to the compound (1) or its salt. In a case where a solvent mixture of an alcohol solvent with an acid (A) is used as the solvent mixture, the amount of the acid (A) is preferably from 0.1 to 10 times by mol, more preferably from 0.5 to 2 times by mol, particularly preferably from 1.0 to 1.3 times by mol, relative to the compound (1) or its salt.

The method 2 is preferably carried out by either one of the following operations methods.

Method 2-1: A method wherein the compound (1) or its salt is dissolved, dispersed or suspended in a protic solvent, and then, a metal or a metal salt is added and reacted. In this method, the metal or the metal salt may be added all at once at the initial stage of the reaction or may be added dividedly in a plurality of times.

Method 2-2: A method wherein a metal or a metal salt is dissolved, dispersed or suspended in a protic solvent, and then, the compound (1) or its salt is dropwise added and reacted. In this method, it is preferred that the compound (1) or its salt is dropwise added in the form of a solution or suspension diluted with a protic solvent, whereby the reaction heat can be suppressed.

The method 2 is preferably carried out by the method 2-2, whereby the operation is good, and control of the reaction will be easy.

Method 3: A method for a reaction with a hydride reactant, such as a metal hydride such as a trialkyltin hydride or a trialkylsilane, or a metal/hydrogen complex compound such as sodium borohydride or lithium aluminum hydride.

In the method 3, the amount of the hydride reactant is preferably from 0.6 to 10 times by mol, particularly preferably from 0.8 to 5 times by mol, relative to the compound (1) or its salt.

The reduction method of the present invention is carried out preferably by the method 2 among them. According to the reduction reaction of the present invention, the chlorine atom at the 6-position of the compound (1) or its salt, is selectively reduced to form the compound (2) or its salt. However, depending upon the structure of the compound (1) or its salt as the starting material, and reaction conditions, the following compound (3) having both chlorine atoms at the 2- and 6-positions reduced, may sometimes be formed as a by-product (provided that $Z^1$ in the formula (2) and the formula (3) is the same group as $Z^1$ in the formula (1)) However, in a case where the reduction reaction is carried out by the method 2, it is possible to suppress the production of the compound (3) as a by-product. Among the method 2, particularly preferred is the method 2 wherein a metal is employed.

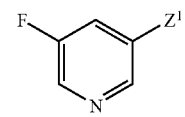

(3)

The reaction temperature for the reduction reaction of the compound (1) or its salt is preferably −20 to +100° C., particularly preferably from −5 to +50° C. The reaction time is not particularly limited. The termination of the reaction may suitably be changed, usually, by analyzing the progress of the reaction by means of high performance liquid chromatography (hereinafter referred to as HPLC) or the like, and the reaction time is preferably from 0.5 to 72 hours, particularly preferably from about 1 to 25 hours.

The crude reaction product obtained as a result of the reduction reaction may be subjected to purification treatment, as the case requires. As a method for such purification treatment, filtration, evaporation of solvent, extraction, washing, high performance liquid chromatography, recrystallization and distillation may, for example, be mentioned.

In the method of the present invention, by utilizing the reactivity of the $Z^1$ group at the 3-position of the compound (2) or its salt obtained by the above reduction reaction, the $Z^1$ group may be converted to another group ($Z^2$ group) thereby to produce the following compound (4) or its salt.

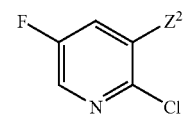

(4)

In the formula (4), $Z^2$ is a group different from $Z^1$ and is a group represented by —$CO_2R^5$, —$CONR^6R^7$ or —CN. From the usefulness of the compound (4) or its salt, $Z^2$ is preferably —$CO_2R^5$. Here, $R^5$ is an alkyl group, an alkenyl group, an aryl group, an aralkyl group or a cycloalkyl group, and each of $R^6$ and $R^7$ which are independent of each other, is a hydrogen atom, an alkyl group, an alkenyl group, an aryl group, an aralkyl group or a cycloalkyl group. $R^5$ is preferably a lower alkyl group, particularly preferably an ethyl group. Each of $R^6$ and $R^7$ which are independent of each other, is preferably a hydrogen atom, a methyl group or an ethyl group, and it is particularly preferred that both $R^6$ and $R^7$ are hydrogen atoms, methyl groups or ethyl groups.

As the method for converting the compound (2) or its salt to the compound (4) or its salt, a known or well known method may be employed and may suitably be selected for use depending upon the types of $Z^1$ and $Z^2$.

For example, the following compound (4a) i.e. the compound (4) wherein $Z^1$ is —$COOR^5$, or its salt, can be produced by an esterification reaction of the following compound (2a-1) i.e. the compound (2) wherein $Z^1$ is —COOH, or its salt, or by an ester exchange reaction of the following compound (2a-2) i.e. the compound (2) wherein $Z^1$ is —$COOR^{10}$ (wherein $R^{10}$ is an alkyl group), or its salt.

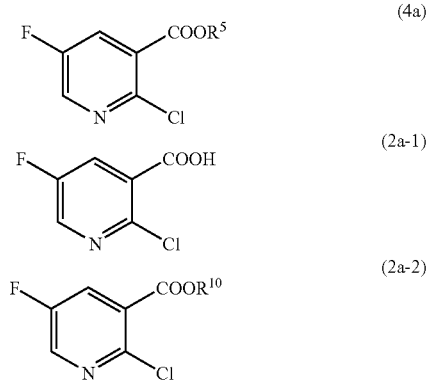

The esterification reaction of the compound (2a-1) or its salt can be carried out by the following method 4-1 or 4-2, preferably the method 4-1, whereby the reactivity is good.

Method 4-1: A method wherein the compound (2a-1) or its salt is reacted with a chlorination agent to obtain the following compound (5) or its salt, and the compound (5) or its salt, and a compound represented by the formula $R^5OH$ (wherein $R^5$ is as defined above) are subjected to an esterification reaction.

Method 4-2: A method wherein the compound (2a-1) or its salt, and a compound represented by the formula $R^5OH$ (wherein $R^5$ is as defined above) are subjected to an esterification reaction.

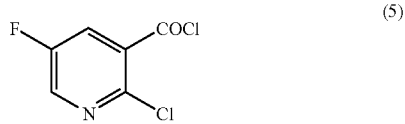

The chlorination agent in the method 4-1 is preferably thionyl chloride or oxalyl chloride, particularly preferably thionyl chloride. The amount of the chlorination agent is preferably from 1 to 10 times by mol relative to the compound (2a-1) or its salt, particularly preferably from 1 to 2 times by mol, since the post treatment is thereby simple.

The chlorination reaction may be carried out in the presence or absence of the solvent, preferably in the presence of a solvent. The solvent may suitably be selected from solvents inert to the chlorination reaction, and an aromatic hydrocarbon solvent such as toluene or xylene, or a halogenated hydrocarbon solvent such as methylene chloride or HFC-225, may, for example, be mentioned. Among these solvents, an aromatic hydrocarbon solvent such as xylene or toluene is preferred.

Further, in order to let the chlorination reaction proceed smoothly, it is preferred to add N,N-dimethylformamide. The amount of the N,N-dimethylformamide is preferably from 0.001 to 1 time by mol, particularly preferably from 0.001 to 0.5 time by mol, relative to the compound (2a-1) or its salt.

The temperature for the chlorination reaction is preferably from +20 to +100° C., particularly preferably from +50 to +90° C.

The time for the chlorination reaction may suitably be changed depending upon the progress of the reaction, and it is preferably from 1 to 24 hours, particularly preferably from 5 to 15 hours, in an industrial production.

In the esterification reaction of the compound (5) or its salt, and the compound represented by the formula $R^5OH$ (wherein $R^5$ is as defined above), the amount of the compound represented by the formula $R^5OH$ is preferably from 1 to 100 times by mol, more preferably from 1 to 20 times by mol, particularly preferably from 1 to 10 times by mol, relative to the compound (5) or its salt.

The esterification reaction may be carried out in the presence or absence of a solvent, preferably in the presence of a solvent. The solvent may be suitably selected from solvents inert to the esterification reaction, and an aromatic hydrocarbon solvent such as toluene or xylene; an aliphatic hydrocarbon solvent such as hexane or heptane; a halogenated hydrocarbon solvent such as HCFC-225 or methylene chloride; or an ether solvent such as diisopropyl ether or tert-butyl methyl ether, may, for example, be mentioned, and an aromatic hydrocarbon solvent such as toluene or xylene is preferred.

The temperature for the esterification reaction is preferably from +50 to +120° C., particularly preferably from +70 to +90° C.

For the esterification reaction, the compound (5) or its salt isolated from the crude reaction solution obtained by the above chlorination reaction may be employed, or the crude reaction solution may be employed as it is. In the latter case, the reaction may be carried out by using the same reactor as the reactor used for the chlorination reaction. As an example of the latter method, a method may be mentioned wherein the compound (2a-1) or its salt is dissolved or suspended in a solvent, and a chlorination agent is added, followed by heating to obtain the compound (5) or its salt, and then the compound represented by the formula $R^5OH$ is dropwise added thereto.

The reaction time for the esterification reaction may be suitably changed depending upon the progress of the reaction, and in an industrial production, the reaction time is preferably from 3 to 20 hours, particularly preferably from 4 to 15 hours.

The esterification reaction in the method 4-2 may be carried out in accordance with the esterification reaction in the method 4-1, and in the method 4-2, it is preferred to use an acid catalyst. The acid catalyst is preferably a Lewis acid or a protic acid, and from the viewpoint of the economical efficiency, a protic acid is preferred. The protic acid may, for example, be concentrated sulfuric acid, hydrochloric acid, p-toluene sulfonic acid or trifluoromethanesulfonic acid, and concentrated sulfuric acid is preferred. The amount of the acid catalyst is preferably from 0.001 to 1 time by mol, particularly preferably from 0.01 to 0.6 time by mol, relative to the compound (5) or its salt.

In order to let the esterification reaction proceed smoothly, it is preferably carried out while water formed as a by-product is distilled off from the reaction system.

The time for the esterification reaction may suitably be changed depending upon the progress of the reaction, and in an industrial production, it is preferably from 1 to 24 hours, particularly preferably from 5 to 15 hours.

The ester exchange reaction of the compound (2a-2) or its salt can be carried out by reacting the compound (2a-2) or its salt with the compound represented by the formula $R^5OH$ (wherein $R^5$ is as defined above), and can be carried out in the same manner as for the esterification reaction disclosed in the method 4-2. In the ester exchange reaction, in order to let the reaction proceed smoothly, it is preferably carried out while the compound represented by the formula $R^{10}H$, formed as a by-product, is distilled off from the reaction system.

The reaction time for the ester exchange reaction may suitably be changed depending upon the progress of the reaction, and in an industrial production, it is preferably from 1 to 24 hours, particularly preferably from 5 to 15 hours.

In the reduction reaction of the present invention, when the compound (1) is used as the starting material, the product may be the compound (2) or a salt of the compound (2), and when a salt of the compound (1) is used as the starting material, the product may be the compound (2) or a salt of the compound (2). Further, depending upon the reaction conditions for the reduction reaction, the product may be the compound (2) only, a salt of the compound (2) only, or a mixture of the compound (2) and a salt of the compound (2).

The same applies to the substitution reaction of the present invention. Namely, when the compound (2) is used as the starting material, the product may be the compound (4) or a salt of the compound (4), and when a salt of the compound (2) is used as the starting material, the product may be the compound (4) or a salt of the compound (4). Further, depending upon the reaction conditions of the substitution reaction, the product may be the compound (4) only, a salt of the compound (4) only, or a mixture of the compound (4) and a salt of the compound (4). The compounds (1) to (4) and salts corresponding thereto, are equivalent compounds showing similar reactivities in the respective reactions in the methods of the present invention.

In a case where the product in the method of the present invention is a compound forming no salt (hereinafter referred to also as a free compound) or its salt, or a mixture thereof, it can be converted to the respective corresponding salt or free compound by a conventional method. For example, as a method for converting a free compound to its salt, a method may be mentioned wherein an acid (hereinafter referred to as an acid (B)) is reacted to the compound (2) or (4) to convert it to a salt of the corresponding compound (2) or (4) (hereinafter referred to also as an acid treatment step) As the acid (B), hydrochloric acid, sulfuric acid, nitric acid, formic acid, acetic acid, trifluoroacetic acid or citric acid may, for example, be mentioned, and hydrochloric acid is preferred. The amount of the acid (B) is preferably from 1 to 10 times by mol, particularly preferably from 1 to 2 times by mol, relative to the compound (2).

The step of reacting the compound (2) with the acid (B) is preferably carried out in the presence of a solvent, whereby stirring and control of heat generation may be facilitated. Such a solvent is a solvent not involved in the reaction and is preferably water or a water-soluble organic solvent. The water-soluble organic solvent may, for example, be an alcohol solvent such as methanol, ethanol or isopropyl alcohol; or a nitrile solvent such as acetonitrile or propionitrile. These solvents may be used alone or in combination as a solvent mixture of two or more of them. As the solvent for the acid treatment step, water, an alcohol solvent or a solvent mixture of water and an alcohol solvent, is preferred, and water, methanol or a solvent mixture of water and methanol, is particularly preferred.

The acid treatment step is preferably carried out by dropwise adding the acid (B) to a solution having the compound (2) dissolved in the solvent. If the compound (2) is precipitated at the time of the dropwise addition of the acid (B), stirring may become difficult, or the purity of the desired compound (2) is likely to be low.

The compound (2) to be used for the acid treatment step may be the compound (2) isolated from the crude reaction solution obtained by the above reduction reaction, or the compound (2) contained in such a crude reaction solution. It is preferably the latter, since the operation can be thereby simplified. In the latter, in a case where the solvent to be used for the acid treatment step is different from the protic solvent used in the reduction step, it is preferred that with respect to the crude reaction solution after completion of the reduction step, the solvent substitution operation is carried out, or the crude reaction solution is concentrated to such a degree that it will not be solidified, and the solvent for the acid treatment step is added, and then, the acid is dropwise added. Whereas, in a case where the solvent to be used for the acid treatment step is the same as the protic solvent used in the reduction step, the acid (B) may be dropwise added after concentrating the crude reaction solution to such a degree that it will not be solidified, or the acid (B) may be dropwise added to the crude reaction solution from the reduction step.

In the acid treatment step, the temperature at the time of the dropwise addition of the acid (B) is preferably from +30 to +100° C., particularly preferably from +40 to +80° C.

The salt of the compound (2) obtained in the acid treatment step is preferably purified, as the case requires. The purification method may suitably be selected from methods such as distillation, sublimation and crystallization, depending upon the physical properties of the salt of the compound (2).

For example, as a method for producing a salt of the compound (2a-1) from the compound (2a-1), the compound (2a-1) is dissolved in a solvent mixture of water and methanol under heating at a level of from +50 to +60° C., and hydrochloric acid is dropwise added to the solution. Then, the content is cooled to a temperature of from +25 to +35° C., whereby a salt of the compound (2a-1) will precipitate. Further, the solution is maintained at that temperature for from 1 to 24 hours to sufficiently precipitate the salt. Then, the precipitate is separated from the mother liquor by a method such as filtration or centrifugal separation, then washed and dried to isolate the salt of the compound (2a-1).

The step of reacting the compound (4) with the acid (B) can be carried out in the same manner as the step of reacting the compound (2) with the acid (B). For example, the method of converting the compound (2a-1) to a salt of the compound (2a-1) can be employed also as a method of converting the compound (4) to a salt of the compound (4).

As a method for converting a salt of the compound to a free compound, a method may be mentioned wherein a salt of the compound (2) or (4) is reacted with a basic compound to convert it to the compound (2) or (4), respectively. The basic compound may, for example, be an inorganic base, such as an alkali metal hydroxide such as sodium hydroxide, potassium hydroxide or lithium hydroxide, or an alkali metal carbonate such as sodium carbonate or potassium carbonate, or an organic base such as triethylamine or pyridine. From the viewpoint of the handling efficiency and the economical efficiency, an inorganic base is preferred, and an alkali metal carbonate such as sodium carbonate or potassium carbonate, is particularly preferred. Such an inorganic base is preferably used in the form of an aqueous solution.

The compound (2) or its salt, and the compound (4) or its salt, obtained by the methods of the present invention, are compounds useful as intermediates for pharmaceuticals, agricultural chemicals, etc. or as intermediates for production of various functional materials.

As a preferred embodiment of the present invention, a method for producing the following compound (4a-1) may be mentioned. Namely, it is a method wherein a compound (1a-1) is reduced by reacting it with a protic solvent in the presence of zinc to obtain a compound (2a-1), then the compound (2a-1) is reacted with hydrochloric acid to obtain a salt of the compound (2a-1), and then the salt of the compound (2-1) is reacted with thionyl chloride and then with ethanol to obtain the compound (4a-1).

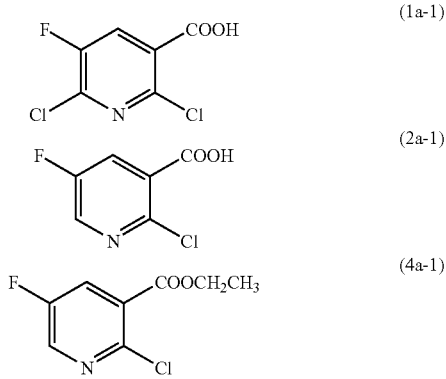

EXAMPLES

Now, the present invention will be described in further detail with reference to Examples, but the present invention is by no means restricted to these Examples. In the following, "%" in the analytical results by HPLC represents area % of each peak in the chromatogram. As the detector for HPLC, an ultraviolet absorption detector was employed. The detection wavelength was 254 nm in Examples 1 to 4 and Reference Example. Further, in Examples 5 and 6, the detection wavelength was 276 nm, and the analytical values were corrected based on the differences in the absorption coefficient depending upon the compounds.

Example 1

Preparation of 2-chloro-5-fluoronicotinic acid (First Example)

Into a 50 mL round bottomed flask, 2,6-dichloro-5-fluoronicotinic acid (1 g), acetic acid (5 mL) and water (0.5 mL) were charged, and under cooling with ice, zinc powder (200 mg) was added, followed by stirring at room temperature for 3 hours. Then, zinc powder (200 mg) was added, followed by stirring for one hour, and then zinc powder (400 mg) was further added, followed by stirring for 3 hours. Further, zinc powder (200 mg) was added, followed by stirring for one hour and then by filtration with celite and washing with ethyl acetate and ethanol. The solvent was distilled off under reduced pressure, and ethyl acetate (20 mL) and a saturated sodium bicarbonate aqueous solution (10 mL) were added for liquid separation. The aqueous layer was extracted three times with ethyl acetate (20 mL). The extract was dried over magnesium sulfate and then concentrated under reduced pressure to obtain a reddish brown oil (400 mg). As a result of the HPLC analysis, the formed reddish brown oil was found to be a mixture comprising 71% of the title compound, 27% of the starting material and 2% of 5-fluoronicotinic acid. Yield: 48%.

$^1$HNMR (CD$_3$OD): δ (ppm) 7.86 (dd, J=7.8, 3.0 Hz, 1H), 8.29 (d, J=2.7 Hz, 1H)

Example 2

Preparation of 2-chloro-5-fluoronicotinic acid (Second Example)

Into a 200 mL round bottomed flask, 2,6-dichloro-5-fluoronicotinic acid (1 g), methanol (10 mL), triethylamine (0.96 g) and 5% Pd/calcium carbonate (one poisoned by lead) (107 mg) were charged under cooling with ice and stirred at room temperature for one hour in a hydrogen atmosphere. The catalyst was filtered off, and the filtrate was concentrated to obtain a crude product (1.3 g). The concentrated filtrate was analyzed by HPLC and found to be a mixture comprising 26% of the title compound, 57% of 2,6-dichloro-5-fluoronicotinic acid and 17% of 5-fluoronicotinic acid.

Example 3

Preparation of ethyl 2-chloro-5-fluoronicotinate (First Example)

Into a 500 mL four-necked flask, ethyl 2,6-dichloro-5-fluoronicotinate (20 g) was put and dissolved by adding acetic acid (190 mL) and water (10 mL). Under cooling with ice, zinc powder (4 g) was added, followed by stirring at room temperature for 0.5 hour. Then, zinc powder (4 g) was added, followed by stirring for 0.5 hour, and zinc powder (4 g) was further added, followed by stirring for 0.5 hour. The solvent was distilled off under reduced pressure, and a 5% sodium bicarbonate aqueous solution (100 mL) and ethyl acetate (100 mL) were added for liquid separation. The aqueous layer was extracted twice with ethyl acetate (100 mL). The organic layer was washed with a 5% sodium bicarbonate aqueous solution (100 mL) and washed with a saturated sodium chloride aqueous solution (100 mL). The solvent was distilled off to obtain a reddish brown oil (15.6 g). It was purified by distillation under reduced pressure to obtain the title compound (10.6 g, yield: 62%). As a result of the HPLC analysis, the purity of the title compound was 99%.

$^1$HNMR (CDCl$_3$): δ (ppm) 1.43 (t, J=7.2 Hz, 3H), 4.43 (q, J=7.2 Hz, 2H), 7.91 (dd, J=7.8, 2.7 Hz, 1H), 8.39 (d, J=3.0 Hz, 1H)

$^{19}$FNMR (CDCl$_3$): δ (ppm)-129.2 (d, J=7.6 Hz)

Example 4

Preparation of 2-chloro-5-fluoronicotinonitrile

Into a 50 mL round bottomed flask, 2,6-dichloro-5-fluoronicotinonitrile (1 g), acetic acid (5 mL) and water (0.5 mL) were charged, and reacted and post-treated in the same manner as in Example 1 and then purified by silica gel column chromatography (hexane/ethyl acetate=6/1) to obtain the title compound (420 mg, yield: 52%). As a result of the HPLC analysis, the purity was 100%.

$^1$HNMR (CDCl$_3$): δ (ppm) 7.76 (dd, J=7.2, 3.0 Hz, 1H), 8.49 (d, J=3.3 Hz, 1H)

$^{19}$FNMR (CDCl$_3$): δ (ppm)-126.9 (d, J=7.6 Hz)

Example 5

Preparation of ethyl 2-chloro-5-fluoronicotinate (Second Example)

Example 5-1

Preparation of a salt of 2-chloro-5-fluoronicotinic acid

Into a 2 L round bottomed flask, zinc powder (847 g) and methanol (4,080 mL) were charged and dispersed with stirring. A methanol (2,720 mL) solution of 2,6-dichloro-5-fluoronicotinic acid (1,700 g) was slowly added dropwise thereto, and then, acetic acid (535 g) was further added dropwise thereto. The internal temperature was raised to 35° C., followed by stirring at that temperature for 5 hours. After confirming that the starting material became at most 3% by the HPLC analysis, the residue of zinc powder was removed by filtration. Methanol was distilled off under reduced pressure, and then, water (3,000 mL) was added, whereby crystals precipitated. Then, the crude reaction product containing the crystals was transferred to a 20 L reactor by means of water (3,750 mL). The internal temperature was heated to at least 50° C., and then, 6 mol/L hydrochloric acid (1,960 g) was dropwise added thereto. After stirring for 3 hours as it was, the mixture was gradually cooled to room temperature, and a precipitated solid was collected by filtration and washed with water. The obtained crystals were dried under reduced pressure (60° C., 30.7 Pa, 12 hours) to obtain a salt of 2-chloro-5-fluoronicotinic acid (1,000 g).

NMR spectrum of the salt of 2-dichloro-5-fluoronicotinic acid:

$^1$HNMR (CD$_3$COCD$_3$): δ (ppm) 8.05 (dd, J=2.9, 8.2 Hz, 1H), 8.47 (d, J=2.9 Hz, 1H)

$^{19}$FNMR (CDCl$_3$): δ (ppm)-130.4 (d, J=9.2 Hz)

Example 5-2

Esterification Reaction of the Salt of 2-chloro-5-fluoronicotinic acid

Into a 5 L four-necked flask, the salt (1,000 g) of 2-chloro-5-fluoronicotinic acid obtained in Example 5-1 was put and dissolved by adding toluene (3,000 mL), thionyl chloride (617 g) and N,N-dimethylformamide (0.95 g). The flask was heated by dipping it in an oil bath set at 80° C. Six hours later, after confirming by the HPLC analysis that 2-chloro-5-fluoronicotinic acid became at most 5%, ethanol (2,173 g) was added. The temperature of the oil bath was raised to 95° C., and the reaction was carried out for 14 hours. Then, concentration under reduced pressure was carried out, and to the obtained crude liquid, ethyl acetate (4,000 mL) and a 7.5% sodium carbonate aqueous solution (4,000 mL) were added, followed by stirring. After confirming that the pH of the aqueous layer was at least 8, filtration and separation were carried out, and an organic layer was recovered. An aqueous layer was extracted with ethyl acetate (2,000 mL), and the extract was put together with the previous organic layer, followed by washing with water (2,000 mL) and then with a 5% sodium chloride aqueous solution (2,000 mL). The organic solvent was distilled off under reduced pressure to obtain a reddish brown oil (1,234.7 g). It was purified by distillation under reduced pressure to obtain ethyl 2-chloro-5-fluoronicotinate (624.8 g). The yield from 2,6-dichloro-5-fluoronicotinic acid was 66%. As a result of the HPLC analysis, the purity of ethyl 2-chloro-5-fluoronicotinate was 99%.

Example 6

Preparation of a salt of 2-chloro-5-fluoronicotinic acid (Second Example)

The reaction and post-treatment were carried out in the same manner as in Example 5-1 except that the internal temperature at the time of dropwise addition of 6 mol/L hydrochloric acid was changed to at least 60° C., and after completion of the dropwise addition, the internal temperature was further heated to 80° C., and stirring was continued at that temperature for 30 minutes, whereby a salt of 2-chloro-5-fluoronicotinic acid (1,000 g) was obtained.

Reference Example

Preparation of a 5-fluoronicotinic acid

Into a 200 mL eggplant type flask, 2,6-dichloro-5-fluoronicotinic acid (1 g), methanol (10 mL), triethylamine (0.96 g) and 5% Pd—C (107 mg) were charged under cooling with ice and stirred at room temperature for 4 hours in a hydrogen atmosphere. After completion of the stirring, Pd—C was filtered off, and the filtrate was concentrated. The obtained crude product was analyzed by HPLC and as a result, found to be a mixture containing 98.6% of the above-identified compound and 1.4% of 2-chloro-5-fluoronicotinic acid.

INDUSTRIAL APPLICABILITY

The present invention provides a method for selectively producing a 3-substituted 2-chloro-5-fluoro-pyridine or its salt by a single step reduction reaction from a readily available 3-substituted 2,6-dichloro-5-fluoro-pyridine or its salt. The reduction reaction can be carried out without using a special reagent and without employing a special reaction condition, and the yield is high. Thus, the method is very advantageous for industrial operation. Further, the 3-substituted 2-chloro-5-fluoro-pyridine or its salt obtained by the above reduction reaction may be subjected to conversion of the substituent by utilizing the reactivity of the substituent at the 3-position. Thus, the present invention may provide efficient methods for producing various 3-substituted 2-chloro-5-fluoro-pyridines or their salts.

The entire disclosure of Japanese Patent Application No. 2003-132137 filed on May 9, 2003 including specification, claims and summary is incorporated herein by reference in its entirety.

What is claimed is:

1. A method for producing a compound represented by the following formula (2) or its salt, which comprises selectively reducing a chlorine atom at the 6-position of a compound represented by the following formula (1) or its salt, provided that in the following formulae, $Z^1$ is a group represented by —CO$_2$R$^1$, —CONR$^2$R$^3$ or —CN, wherein each of R$^1$, R$^2$ and R$^3$ which are independent of one another, is a hydrogen atom, an alkyl group, an alkenyl group, an aryl group, an aralkyl group or a cycloalkyl group:

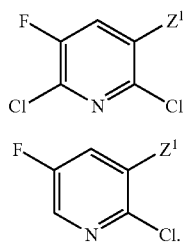

2. A method for producing a compound represented by the following formula (2), which comprises selectively reducing a chlorine atom at the 6-position of a compound represented by the following formula (1), provided that in the following formulae, $Z^1$ is a group represented by $CO_2R^1$, $-CONR^2R^3$ or $-CN$, wherein each of $R^1$, $R^2$ and $R^3$ which are independent of one another, is a hydrogen atom, an alkyl group, an alkenyl group, an aryl group, an aralkyl group or a cycloalkyl group:

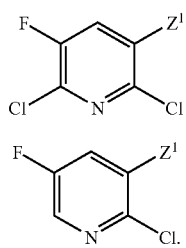

3. The method according to claim 1, wherein $Z^1$ is $CO_2R^1$ (wherein $R^1$ is as defined above).

4. The method according to claim 1, wherein the reduction is carried out by letting a protic solvent act in the presence of a metal or a metal salt.

5. The method according to claim 1, wherein the reduction is carried out by letting a protic solvent act in the presence of zinc.

6. A method for producing a compound represented by the following formula (4) or its salt, which comprises carrying out a substitution reaction of a compound represented by the formula (2) or its salt obtained by the method as defined in claim 1, to substitute the $Z^1$ group at the 3-position by a $Z^2$ group, thereby to obtain a compound represented by the following formula (4) or its salt, provided that $Z^2$ in the following formula is a group different from $Z^1$ and is a group represented by $-CO_2R^5$, $-CONR^6R^7$ or $-CN$, wherein $R^5$ is an alkyl group, an alkenyl group, an aryl group, an aralkyl group, or a cycloalkyl group, and each of $R^6$ and $R^7$ which are independent of each other, is a hydrogen atom, an alkyl group, an alkenyl group, an aryl group, an aralkyl group or a cycloalkyl group:

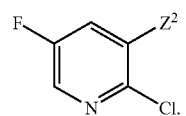

7. The method according to claim 6, wherein from the compound of the formula (2) or its salt wherein the $Z^1$ group is a group represented by $-COOH$ or $-COOR^{10}$ (wherein $R^{10}$ is an alkyl group), the compound (4) wherein $Z^2$ is a $-COOR^5$ group (wherein $R^5$ is as defined above), is obtained by an esterification reaction in a case where $Z^1$ is a $-COOH$ group, or by an ester exchange reaction in a case where $Z^1$ is a $-COOR^{10}$ group (wherein $R^{10}$ is as defined above).

8. The method according to claim 3, wherein $R^1$ is a hydrogen atom.

9. The method according to claim 1, wherein $Z^1$ is $-CONR^2R^3$ wherein $R^2$ and $R^3$, independently of each other, are selected from the group consisting of a hydrogen atom, a methyl group and an ethyl group.

10. The method according to claim 1, wherein the compound of formula (I) is selected from the group consisting of 2,6-dichloro-5-fluoronicotinic acid, methyl 2,6-dichloro-5-fluoronicotinate, ethyl 2,6-dichloro-5-fluoronicotinate, isopropyl 2,6-dichloro-5-fluoronicotinate, butyl 2,6-dichloro-5-fluoronicotinate, 2,6-dichloro-5-fluoronicotinonitrile, 2,6-dichloro-5-fluoronicotinic acid amide, 2,6-dichloro-5-fluoronicotinic acid dimethylamide, 2,6-dichloro-5-fluoronicotinic acid diethylamide, and 2,6-dichloro-5-fluoro-3-cyanopyridine.

11. The method according to claim 1, wherein the compound of formula (I) is 2,6-dichloro-5-fluoronicotinic acid.

12. The method according to claim 1, wherein reducing includes carrying out a catalytic hydrogenolysis with hydrogen in the presence of a metal reduction catalyst.

13. The method according to claim 1, wherein the reducing is carried out in the presence of a protic solvent and at least one of sodium and lithium.

14. The method according to claim 1, wherein the reducing is carried out by reacting the compound of formula (I) with a hydride reactant.

15. The method according to claim 14, wherein the hydride reactant is at least one selected from the group consisting of a trialkyl tin hydride, a trialkyl silane, sodium borohydride, and lithium aluminum hydride.

16. The method according to claim 2, wherein $Z^1$ is $-CONR^2R^3$ wherein $R^2$ and $R^3$, independently of each other, are selected from the group consisting of a hydrogen atom, a methyl group and an ethyl group.

17. The method according to claim 2, wherein the compound of formula (I) is selected from the group consisting of 2,6-dichloro-5-fluoronicotinic acid, methyl 2,6-dichloro-5-fluoronicotinate, ethyl 2,6-dichloro-5-fluoronicotinate, isopropyl 2,6-dichloro-5-fluoronicotinate, butyl 2,6-dichloro-5-fluoronicotinate, 2,6-dichloro-5-fluoronicotinonitrile, 2,6-dichloro-5-fluoronicotinic acid amide, 2,6-dichloro-5-fluoronicotinic acid dimethylamide, 2,6-dichloro-5-fluoronicotinic acid diethylamide, and 2,6-dichloro-5-fluoro-3-cyanopyridine.

18. The method according to claim 2, wherein the compound of formula (I) is 2,6-dichloro-5-fluoronicotinic acid.

19. The method according to claim 2, wherein the reducing includes carrying out a catalytic hydrogenolysis with hydrogen in the presence of a metal reduction catalyst.

20. The method according to claim 2, wherein the reducing is carried out in the presence of a protic solvent and at least one of sodium and lithium.

21. The method according to claim 2, wherein the reducing is carried out by reacting the compound of formula (I) with a hydride reactant.

22. The method according to claim 21, wherein the hydride reactant is at least one selected from the group consisting of a trialkyl tin hydride, a trialkyl silane, sodium borohydride, and lithium aluminum hydride.

23. The method according to claim 1, wherein the reducing is carried out by directly replacing the chlorine atom with a hydrogen atom.

24. The method according to claim 2, wherein the reducing is carried out by directly replacing the chlorine atom with a hydrogen atom.

25. The method according to claim 1, wherein the reducing is carried out in one step.

26. The method according to claim 2, wherein the reducing is carried out in one step.

* * * * *